United States Patent
Allison et al.

(10) Patent No.: US 6,355,242 B1
(45) Date of Patent: *Mar. 12, 2002

(54) MATERIALS AND METHODS FOR TREATING OR PREVENTING OXALATE-RELATED DISEASE

(75) Inventors: Milton J. Allison, Ames, IA (US); Harmeet Sidhu, Gainesville, FL (US)

(73) Assignee: Ixion Biotechnology, Inc., Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/500,500

(22) Filed: Feb. 9, 2000

Related U.S. Application Data

(63) Continuation-in-part of application No. 09/083,362, filed on May 22, 1998, now Pat. No. 6,200,562.
(60) Provisional application No. 60/150,259, filed on Aug. 23, 1999, and provisional application No. 60/047,473, filed on May 23, 1997.

(51) Int. Cl.$^7$ ................................................ A01N 63/00
(52) U.S. Cl. ..................... 424/93.4; 424/93.1; 424/94.1; 424/94.5; 435/183; 435/193; 435/196; 435/252.1
(58) Field of Search ............................... 424/94.1, 93.4, 424/94.5, 93.1; 435/183, 252.1, 193, 196

(56) References Cited

U.S. PATENT DOCUMENTS

| | | |
|---|---|---|
| 5,286,495 A | 2/1994 | Batich et al. |
| 5,547,870 A | 8/1996 | Datta et al. |
| 5,604,111 A | 2/1997 | Peck |

FOREIGN PATENT DOCUMENTS

| | | |
|---|---|---|
| WO | 9531537 | 11/1995 |
| WO | 9535377 | 12/1995 |
| WO | 9816632 | 4/1998 |

OTHER PUBLICATIONS

Allison, M.J., H.M. Cook (1981) "Oxalate degradation by microbes of the large bowel of herbivores: the effect of dietary oxalate" Science 212:675–676.

Allison, Milton J., Karl A. Dawson, William R. Mayberry, John G. Foss (1985) "*Oxalobacter formigens* gen. nov., sp. now.: oxalate–degrading anaerobes that inhibit the gastrointestinal tract" Arch Microbiol 141:1–7.

Allison, Milton J., Herbert M. Cook, David B. Milne, Sandra Gallagher, Ralph V. Clayman (1986) "Oxalate Degradation by Gastrointestinal Bacteria from Humans" J. Nutr. 116:455–460.

Allison, Milton J., Steven L. Daniel, Nancy A. Cornick (1995) "Oxalate–Degrading Bacteria" In: Khan, S.R. (ed), Calcium Oxalate in Biological Systems CRC Press, Chapter 7, pp. 131–168.

Daniel, S.L., P.A. Hartman, M.J. Allison (1993) "Intestinal Colonisation of Laboratory Rats by Anaerobic Oxalate–degrading Bacteria: Effects on the Urinary and Faecal Excretion of Dietary Oxalate" Microbial Ecology in Health and Disease 6:277–283.

Daniel, Steven L., Paul A. Hartman, Milton J. Allison (1987) "Microbial Degradation of Oxalate in the Gastrointestinal Tracts of Rats" Applied and Environmental Microbiology 53(8):1793–1797.

Dawson, Karl A., M.J. Allison, P.A. Hartman (1980) "Isolation and Some Characteristics of Anaerobic Oxalate–Degrading Bacteria from the Rumen" Applied and Environmental Microbiology 40(4):833–839.

Doane, Lori T., Michael Liebman, Daniel R. Caldwell (1989) "Microbial Oxalate Degradation: Effects On Oxalate And Calcium Balance In Humans" Nutrition Research 9:957–964.

Solomons, Clive C., M. Herzl Melmed, Susan M. Heitler (1991) "Calcium Citrate For Vulvar Vestibulitis" The Journal of Reproductive Medicine 36(12):879–882.

Sidhu, H., M.J. Allison, A.B. Peck (1996) "Detection and Characterization of *Oxalobacter formigenes* Strains Using Oligonucleotide Probes" Meeting for Urolithaisis, pp 537–539, Pak, C.Y.C. et al. (ed.).

Ito, Haruo, Masami Miyake, Masatoshi Noda (1995) "A New Oxalate–degrading Organism Isolated from Human Feces" Abstr. Annual Meeting Amer. Soc. Microbiol. Q–106.

Jensen, Neil S., Milton J. Allison (1994) Studies on the Diversity Among Anaerobic Oxalate Degrading Bacteria now in the Species *Oxalobacter formigenes* Abstr. General Meeting of the American Soc. Microbiol. I–12.

Lung, Hui–Yu et al. (1991) Cloning and expression of the oxalyl–CoA decarboxylase gene from the bacterium, *Oxalobacter formigenes*: prospects for gene therapy to control Ca–oxalate kidney stone formation American Journal of Kidney Disease vo.I. XVII (4): 381–385.

Han, Jian–zhi et al. (1995) "The Relationships of *Oxalobacter Formigenes* and Calcium Oxalate Calculi" Journal of Tongji Medical University 15(4):249–252.

*Primary Examiner*—Leon B. Lankford, Jr.
(74) *Attorney, Agent, or Firm*—Saliwanchik, Lloyd & Saliwanchik

(57) ABSTRACT

This invention provides materials and procedures for the delivery of selected strains of bacteria and/or oxalate-degrading enzymes to the intestinal tracts of persons and/or domestic or zoological animals who are at increased risk for oxalate related disease because they have lost, or have inadequate concentrations of these bacteria. The administration of these bacteria and/or the relevant enzyme removes oxalate from the intestinal tract and thus reduces the amount of oxalate available for absorption and reduces the risk for oxalate related disease.

25 Claims, 6 Drawing Sheets

MATERIALS AND METHODS FOR TREATING OR PREVENTING OXALATE-RELATED DISEASE

CROSS-REFERENCE TO A RELATED APPLICATION

This application is a continuation-in-part of U.S. application Ser. No. 09/083,362, filed May 22, 1998 now U.S. Pat. No. 6,200,562 which claims the benefit of U.S. Provisional Application No. 60/047,473, filed May 23, 1997. This application also claims the benefit of U.S. Provisional Application No. 60/150,259, filed Aug. 23, 1999.

BACKGROUND OF THE INVENTION

Kidney-urinary tract stone disease (urolithiasis) is a major health problem throughout the world. Most of the stones associated with urolithiasis are composed of calcium oxalate alone or calcium oxalate plus calcium phosphate. Other disease states have also been associated with excess oxalate. These include, vulvodynia, oxalosis associated with end-stage renal disease, cardiac conductance disorders, Crohn's disease, and other enteric disease states.

Oxalic acid (and/or its salt-oxalate) is found in a wide diversity of foods, and is therefore, a component of many constituents in human and animal diets. Increased oxalate absorption may occur after foods containing elevated amounts of oxalic acid are eaten. Foods such as spinach and rhubarb are well known to contain high amounts of oxalate, but a multitude of other foods and beverages also contain oxalate. Because oxalate is found in such a wide variety of foods, diets that are low in oxalate and which are also palatable are hard to formulate. In addition, compliance with a low oxalate diet is often problematic.

Endogenous oxalate is also produced metabolically by normal tissue enzymes. Oxalate (dietary oxalate that is absorbed as well as oxalate that is produced metabolically) is not further metabolized by tissue enzymes and must therefore be excreted. This excretion occurs mainly via the kidneys. The concentration of oxalate in kidney fluids is critical, with increased oxalate concentrations causing increased risk for the formation of calcium oxalate crystals and thus the subsequent formation of kidney stones.

The risk for formation of kidney stones revolves around a number of factors that are not yet completely understood. Kidney-urinary tract stone disease occurs in as much as 12% of the population in Western countries and about 70% of these stones are composed of calcium oxalate or of calcium oxalate plus calcium phosphate. Some individuals (e.g., patients with intestinal disease such as Crohn's disease, inflammatory bowel disease, or steatorrhea and also patients that have undergone jejunoileal bypass surgery) absorb more of the oxalate in their diets than do others. For these individuals, the incidence of oxalate urolithiasis increases markedly. The increased disease incidence is due to increased levels of oxalate in kidneys and urine, and this, the most common hyperoxaluric syndrome in man, is known as enteric hyperoxaluria. Oxalate is also a problem in patients with end-stage renal disease and there is recent evidence (Solomons, C. C., M. H. Melmed, S. M. Heitler [1991] "Calcium citrate for vulvar vestibulitis" *Journal of Reproductive Medicine* 36:879–882) that elevated urinary oxalate is also involved in vulvar vestibulitis (vulvodynia).

Bacteria that degrade oxalate have been isolated from human feces (Allison, M. J., H. M. Cook, D. B. Milne, S. Gallagher, R. V. Clayman [1986] "Oxalate degradation by gastrointestinal bacteria from humans" *J Nutr.* 116:455–460). These bacteria were found to be similar to oxalate-degrading bacteria that had been isolated from the intestinal contents of a number of species of animals (Dawson, K. A., M. J. Allison, P. A. Hartman [1980] "Isolation and some characteristics of anaerobic oxalate-degradingbacteria the rumen" *Appl. Environ. Microbiol.* 40:833–839; Allison, M. J., H. M. Cook [1981] "Oxalate degradation by microbes of the large bowel of herbivores: the effect of dietary oxalate" *Science* 212:675–676; Daniel, S. L., P. A. Hartman, M. J. Allison [1987] "Microbial degradation of oxalate in the gastrointestinal tracts of rats" *Appl. Environ. Microbiol.* 53:1793–1797). These bacteria are different from any previously described organism and have been given both a new species and a new genus name (Allison, M. J., K. A. Dawson, W. R. Mayberry, J. G. Foss [1985] "*Oxalabacter formigenes* gen. nov., sp. nov.:oxalate-degradinganaerobes that inhabit the gastrointestinal tract" *Arch. Microbiol.* 141:1–7).

Not all humans carry populations of *O. formigenes* in their intestinal tracts (Allison, M. J., S. L. Daniel, N. A. Comick [1995] "Oxalate-degrading bacteria" In Khan, S. R. (ed.), *Calcium Oxalate in Biological Systems* CRC Press; Doane, L. T., M. Liebman, D. R. Caldwell [1989] "Microbial oxalate degradation: effects on oxalate and calcium balance in humans" *Nutrition Research* 9:957–964). There are low concentrations or a complete lack of oxalate degrading bacteria in the fecal samples of persons who have had jejunoileal bypass surgery (Allison et al. [1986] "Oxalate degradation by gastrointestinal bacteria from humans" *J. Nutr.* 116:455–460). Also, certain humans and animals may maintain colonies of *O. formigenes* but nevertheless have excess levels of oxalate for reasons which are not clearly understood.

BRIEF SUMMARY OF THE INVENTION

The subject invention pertains to materials and methods which reduce the risk for developing oxalate-related disorders by reducing the amount of oxalate in the intestinal tract. This reduction in the intestinal tract leads to a reduction in systemic oxalate levels thereby promoting good health.

In one embodiment of the subject invention, a reduction in oxalate absorption is achieved by supplying oxalate-degrading bacteria to the intestinal tract. In a preferred embodiment, these bacteria are *Oxalobacter formigenes*. These bacteria use oxalate as a growth substrate. This utilization reduces the concentration of soluble oxalate in the intestine and, thus, the amount of oxalate available for absorption. A reduction of oxalate in the intestinal tract can also lead to removal of oxalate from the circulatory system.

In a specific embodiment, the subject invention provides materials and procedures for the delivery of *O. formigenes* to the intestinal tracts of persons who are at increased risk for oxalate-related disease. These bacteria and their progeny replicate in the intestine and remove oxalate from the intestinal tract, thereby reducing the amount of oxalate available for absorption (and/or causing oxalate excretion from the blood into the intestine) and thus reducing the risk for oxalate related disease.

In accordance with the teaching of the subject invention, oxalate-degradingmicrobes other than *O. formigenes* which utilize oxalate as a substrate can also be used to achieve therapeutic oxalate degradation thereby reducing the risk of urolithiasis and other oxalate-related disorders. Such other microbes may be, for example, bacteria such as clostridia or pseudomonads.

In one embodiment of the subject invention, the microbes which are used to degrade oxalate naturally produce enzymes which confer upon these microbes the ability to degrade oxalate. In an alternative embodiment, microbes may be transformed with polynucleotide sequences which confer upon the transformed microbes the ability to degrade oxalate. Specifically, the enzymes formyl—CoA transferase and oxalyl—CoA decarboxylase have been identified as playing a central role in oxalate degradation. In one embodiment of the subject invention, an appropriate host can be transformed with heterologous DNA encoding these enzyme activities thereby conferring upon the transformed host the ability to augment oxalate degradation. The host may be, for example, a microbe which is particularly well adapted for oral administration and/or colonizing the intestines. Alternatively, the host may be a plant which, once transformed, will produce the desired enzyme activities thereby making these activities available in the intestine when the plant material is consumed.

A further embodiment of the subject invention provides plants transformed with oxalate-degrading enzymes wherein these plants have enhanced resistance to fungi which require oxalate for their pathogenesis of plants or which produce oxalic acid as a mechanisms for their pathogenesis of plants.

In a further embodiment of the subject invention, a reduction in oxalate levels is achieved by administering enzymes which act to degrade oxalate. These enzymes may be isolated and purified or they may be administered as a cell lysate. The cell lysate may be, for example, *O. formigenes*. In a specific embodiment, the enzymes which are administered are formyl-CoA transferase and oxalyl-CoA decarboxylase. In a preferred embodiment, additional factors which improve enzyme activity can be administered. These additional factors may be, for example, oxalyl CoA, $MgCl_2$, and TPP (thiamine diphosphate, an active form of vitamin $B_1$).

Thus, in one embodiment of the subject invention, a reduction in oxalate levels is achieved by administering oxalate-degrading enzymes produced by a recombinant microbe, such as *Escherichia coli*, which has been transformed to express oxalate-degrading enzymes. The recombinant host may be administered in either a viable or non-viable form. A further aspect of the subject invention pertains to pharmaceutical compositions and/or nutritional supplements for oral administration. These compositions release the oxalate degrading microbes, or oxalate degrading enzymes, in the intestines of humans or animals. Preferably the microorganisms and/or enzymes are encapsulated in a dose delivery system that decreases the probability of release of the materials in the human or animal stomach but increases the probability of release in the intestines. The microorganisms and/or enzymes also may be administered as a constituent of foods, such as milk, meats, and yogurt.

In a further embodiment of the subject invention, a reduction in oxalate absorption is achieved in domesticated, agricultural, or zool-maintained animals deficient in oxalate-degrading bacteria by administering oxalate-degrading microorganisms, plants, and/or enzymes.

DETAILED DISCLOSURE OF THE INVENTION

Figure 1A:
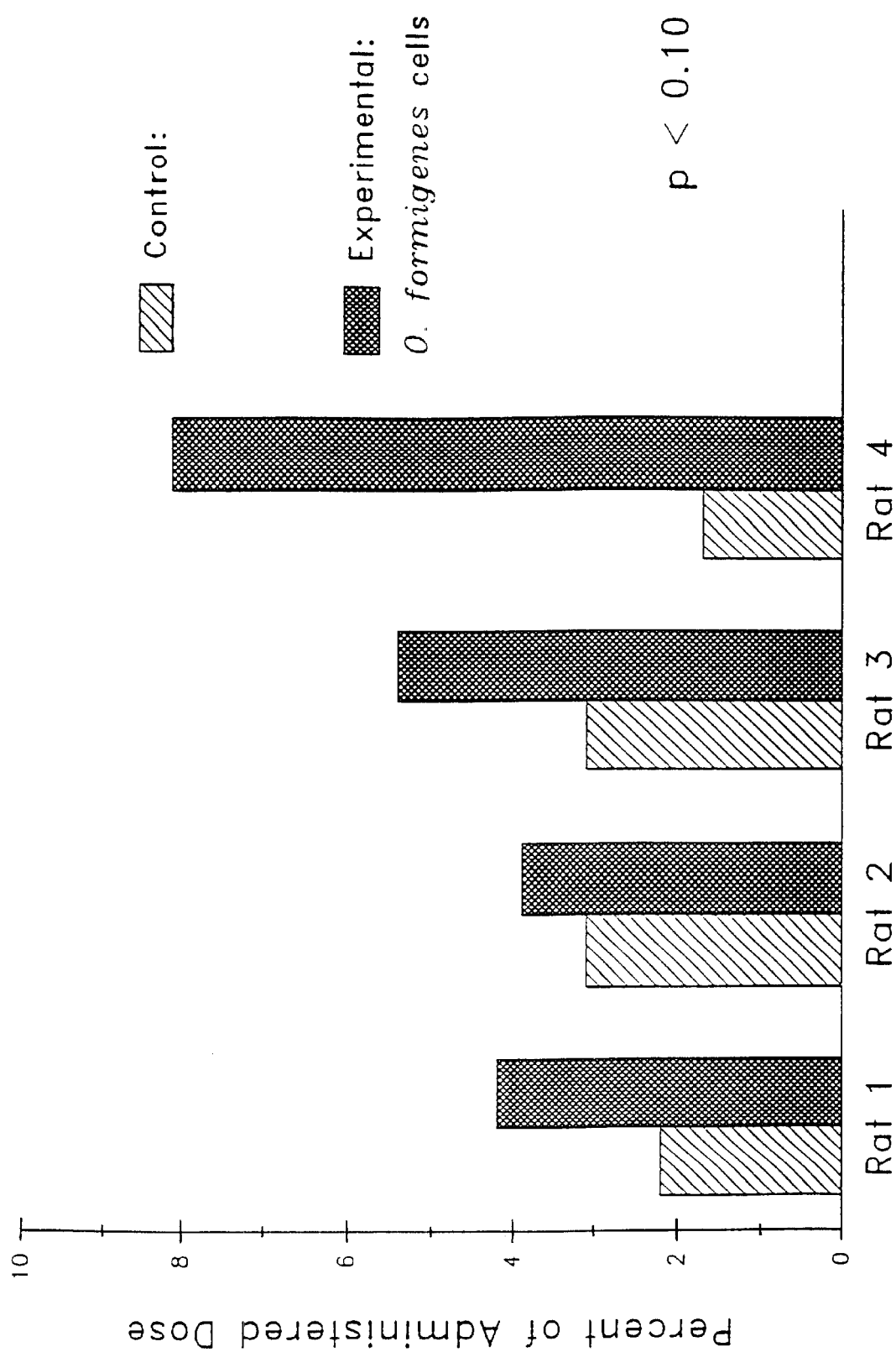
FIG. 1a shows the results of a study evaluating the conversion of labeled carbon (C-14) from dietary oxalate into carbon dioxide when *Oxalobacter formigenes* cells are fed to rats on a high calcium diet.

The subject invention pertains to the introduction of oxalate-degrading bacteria and/or enzymes into a human or animal intestinal tract where the activity of these materials reduces the amount and/or concentration of oxalate present thereby reducing the risk of disease due to oxalate.

In a specific embodiment, the subject invention pertains to the preparation and administration of cells of oxalate-degrading bacteria of the species, *Oxalobacter formigenes*, to the human or animal intestinal tract where the activity of the microbes reduces the amount of oxalate present in the intestine thereby causing a reduction of concentrations of oxalate in the kidneys and in other cellular fluids. The introduced cells degrade oxalate and replicate in the intestinal habitat so that progeny of the initial cells colonize the intestine and continue to remove oxalate. This activity reduces the risk for formation of kidney stones as well as other disease complications caused by oxalic acid. In a preferred embodiment for human use, the specific strains of *O. formigenes* used are strains isolated from human intestinal samples. The strains are thus part of the normal human intestinal bacterial flora. However, since they are not present in all persons, or are present in insufficient numbers, the introduction of these organisms corrects a deficiency that exists in some humans.

Enrichment of the contents of the intestines with one or more species of oxalate-degrading bacteria causes a reduction of oxalate in the intestinal contents. Some of the bacteria carry out oxalate degradation at or near the site of absorption. The activity of the bacteria decreases the level of absorption of dietary oxalate. A reduction in oxalate concentration in the intestines can also lead to a removal of oxalate from cells and the general circulation. More specifically, a reduction of oxalate concentration in the intestines can also lead to enhanced secretion of oxalate into the intestine from the blood and thus reduce the amount of oxalate that needs to be excreted in urine. Thus, the methods of the subject invention can be used to treat primary hyperoxaluria in addition to treatment of dietary hyperoxaluria. The materials and methods of the subject invention are particularly advantageous in the promotion of healthy oxalate levels in humans and animals.

Pharmaceutical and nutriceutical compositions for the introduction of oxalate degrading bacteria and/or enzymes into the intestine include bacteria and/or enzymes that have been lyophilized or frozen in liquid or paste form and encapsulated in a gel capsule or other enteric protection. The gel cap material is preferably a polymeric material which forms a delivery pill or capsule that is resistant to degradation by the gastric acidity and enzymes of the stomach but is degraded with concomitant release of oxalate-degrading materials by the higher pH and bile acid contents in the intestine. The released material then converts oxalate present in the intestine to harmless products. Pharmaceutical or nutriceutical carriers also can be combined with the bacteria or enzymes. These would include, for example, saline-phosphate buffer.

Bacteria and/or enzymes to be administered can be delivered as capsules or microcapsules designed to protect the material from adverse effects of acid stomach. One or more of several enteric protective coating methods can be used. Descriptions of such enteric coatings include the use of cellulose acetate phthalate (CAP) (Yacobi, A., E. H. Walega, 1988, Oral sustained release formulations: Dosing and evaluation, Pergammon Press). Other descriptions of encapsulation technology include U.S. Pat. No. 5,286,495, which is incorporated herein by reference. The compositions of the subject invention can also be formulated as suppositories.

Other methods of administration of these microorganisms and/or enzymes to the intestines include adding the material directly to food sources. The bacteria may be added as freshly harvested cells, freeze dried cells, or otherwise protected cells. Foods may be supplemented with oxalate degrading organisms without affecting their taste or appearance. These foods may be, for example, yogurt, milk, peanut butter or chocolate. Upon ingestion, when the food products are being digested and absorbed by the intestines, the microorganisms and/or enzymes degrade oxalate present in the intestines thus reducing absorption of oxalate into the blood stream.

As noted above, a variety of foods can be supplemented with oxalate degrading microorganisms. As an initial step, the microbes can be grown in media and separated from the media by, for example, centrifugation. Traditional yogurt cultures obtained from a commercial dairy can be mixed with the oxalate degrading microbial culture. This mixture of cultures then can be added to the basic dairy yogurt premix without adversely affecting taste or consistency. The yogurt can then be produced and packaged using traditional commercial procedures. In another example, the oxalate degrading bacteria can be added to already produced yogurts.

Another example is to add the microbes to milk after it has been homogenized and sterilized. Such a method is currently used in the diary industry for adding *Lactobacillus acidophilus* organisms to milk. Any food source containing bacteria can be used by supplementing with oxalate-degrading bacteria. These food products include cheese or meat products that have desirable microorganisms added during processing.

In yet a further embodiment, the subject invention provides a novel enzyme delivery system. This system comprises a plant which has been transformed with heterologous polynucleotide(s) to express oxalate-degradingenzymes. The enzyme-expressing transgenic plant may be administered to patients as a constituent of a salad, for example. Further, the enzyme-expressing plant may be administered to animals as a constituent of feed, for example, or grown in grazing pasture. The animals to which these products may be fed include, for example, cattle, pigs, dogs and cats.

Thus, as an alternative method of administration to the intestine, plants are genetically engineered to express oxalate-degrading enzymes. These transgenic plants are added to the diet, with the activity of the enzymes causing a decrease in the presence of oxalate. DNA sequences encoding these enzymes are known to those skilled in the art and are described in, for example, WO 98/16632.

In addition to plants which can be used as a dietary component to promote healthy oxalate levels in humans or animals, the subject invention provides plants with enhanced resistance to microbial infections. Specifically, the transformed plants of the subject invention are protected against microbes which require or use the presence of oxalate for plant pathogenicity. The plants of the subject invention, which are transformed to express oxalate-degrading enzymes are protected against, for example, certain fungi which need oxalate for pathogenicity. The genes encoding the enzymes can be modified to enhance expression and/or stability in plants. Also, the expression may be under the control of promoters which direct expression in particular tissues.

In one embodiment, the strains of bacteria (*O. formigenes*) used according to the subject invention are pure cultures that are isolated from anaerobic cultures that have been inoculated with dilutions of intestinal contents from normal humans or, for use with animals, from normal animals. A special calcium oxalate containing medium that allows detection of oxalate degrading colonies can be used. In one embodiment, the purity of each strain can be assured through the use of at least two subsequent repetitive cloning steps.

Strains of *O. formigenes* useful according to the subject invention have been characterized based upon several tests, these include: patterns of cellular fatty acids, patterns of cellular proteins, DNA and RNA (Jensen, N. S., M. J. Allison (1995) "Studies on the diversity among anaerobic oxalate degrading bacteria now in the species *Oxalobacter formigenes*" Abstr. to the General Meeting of the Amer. Soc. Microbiol., 1–29), and responses to oligonucleotide probes (Sidhu et al. 1996). Two groups of these bacteria (Groups I and II, both existing within the present description of the species) have been described. Strains used have been selected based upon oxalate degrading capacity, and evidence of the ability to colonize the human intestinal tract. Strains selected include representatives of both Groups I and II of the species.

One embodiment of the present invention involves procedures for selection, preparation and administration of the appropriate oxalate-degrading bacteria to a diversity of subjects. Prominently, but not exclusively, these are persons or animals which do not harbor these bacteria in their intestines. These non-colonized or weakly-colonized persons or animals are identified using tests that allow for rapid and definitive detecting of *O. formigenes* even when the organisms are at relatively low concentrations in mixed bacterial populations such as are found in intestinal contents. The methods of the subject invention can also be used to treat individuals or animals whose oxalate-degrading bacteria have been depleted due to, for example, antibiotic treatment or in post-operative situations. The methods of the subject invention can also be used to treat individuals or animals who have colonies of oxalate-degradingbacteria but who still have unhealthy levels of oxalate due to, for example, oxalate susceptibility and/or excessive production of endogenous oxalate.

Bacteria which can be used according to the subject invention can be identified by at least two methods:

1) Oligonucleotide probes specific for these bacteria can be used; and/or
2) A culture test wherein an anaerobic medium with 10 mM oxalate is inoculated and after incubation at 37° C. for 1 to 7 days, the loss of oxalate is determined.

Pure cultures of *O. formigenes* strains can be grown in large fermenter batch cultures and cells can be harvested using techniques known to those skilled in the art. Cells from a selected single strain or mixtures of known strains can be treated as needed (e.g., freeze dried with trehalose or glycerol) to preserve viability and are then placed in capsules designed to protect the cells through their passage through the acid stomach (enteric coated capsules).

Cells are ingested in quantities and at intervals determined by the needs of individuals. In some cases a single, or periodic, use may be all that is needed and in other cases regular ingestion (e.g., with meals) may be needed.

The invention further pertains to administration to the human or animal intestinal tract of oxalate-degrading products or enzymes prepared from *O. formigenes* cells. In one embodiment, oxalate degrading enzymes can be purified and prepared as a pharmaceutical or nutriceutical composition for oral consumption. In a preferred embodiment, these enzymes are produced recombinantly. DNA sequences encoding these enzymes are known to those skilled in the art and are described in, for example, WO 98/16632. These sequences, or other sequences encoding oxalate-degrading proteins, can be expressed in a suitable host. The host may be, for example, *E. coli* or Lactobacillus. The transformed host would included appropriate regulatory and transporter signals. The expressed protein may be isolated, purified and administered as described herein. Alternatively, the recombinant host expressing the desired oxalate-degrading proteins may be administered. The recombinant host may be administered in either a viable or non-viable form. In another preferred embodiment, the enzymes are coated or otherwise formulated or modified to protect the enzymes so that they are not inactivated in the stomach, and are available to exert their oxalate-degrading activity in the small intestine. Examples of such formulations are known to those skilled in the art and are described in, for example, U.S. Pat. No. 5,286,495.

The use of *O. formigenes* is particularly advantageous because it is an anaerobe that does not grow in aerobic tissue environments and does not produce any compounds which are toxic to humans or animals. As an alternative to either *O. formigenes* or a recombinant host, other oxalate-degrading bacteria may be used, such as Clostridium or Pseudomonas. Oxalate-degrading enzymes prepared from such alternative bacteria may be administered or the entire microbe may be administered.

In addition, all aforementioned embodiments are applicable to domesticated, agricultural, or zoo-maintained animals suffering from deficient numbers of oxalate-degrading bacteria, as well as to humans. For example, oxalate-degrading enzymes and/or microbes may be administered to house pets such as dogs, cats, rabbits, ferrets, guinea pigs, hamsters and gerbils, as well as to agricultural animals, such as horses, sheep, cows and pigs, or wild animals maintained for breeding purposes such as river otters.

Following are examples which illustrate procedures for practicing the invention. These examples should not be construed as limiting.

EXAMPLE 1
Treatment of High Risk Patients

Enteric coated *O. formigenes* cells can be ingested by patient populations at high risk for oxalate related disease. These include:
1. Persons that have a history of urolithiasis with multiple episodes of idiopathic stone disease.
2. Persons at risk for urolithiasis with high urinary oxalate due to enteric disease (enteric-hyperoxaluria).
3. Persons with high serum oxalate levels due to end stage renal disease.
4. Persons with vulvar vestibultitis.
5. Persons that have diets with high levels of oxalate such as found in certain areas and seasons in India and in Saudi Arabia. This would also include individuals who happen to prefer foods such as spinach which are high in oxalate.
6. Persons who produce too much endogenous oxalate due to, for example, a genetic defect.

EXAMPLE 2
Treatment of Low Risk Patients

Enteric protected *O. formigenes* cells can also be ingested by individuals in populations at lower risk for oxalate related disease. These include:
1. Persons that have lost populations of normal oxalate degrading bacteria due to: treatments with oral antibiotics or bouts of diarrheal disease.
2. Infants can be inoculated so that a normal protective population of Oxalabacter will be more easily established than is the case later in life when competitive exclusion principles operate.

EXAMPLE 3
Use of Oxalate Degrading Enzymes From *Oxalobacter formigenes* to Control Hyperoxaluria A study was conducted to evaluate the efficacy of oxalate degrading enzymes from *Oxalobacter formigenes* for the control of hyperoxaluria.

Animals Used: Male Sprague Dawley Rats: BW 250–300 g
Diets Used: Normal Diet (N.D.): Harlan Teklad TD 89222; 0.5% Ca, 0.4%P
Drug Used: Lyophilized mixture of *Oxalobacter formigenes* lysate (source of enzymes) with Oxalyl CoA, $MgCl_2$ and TPP.
Drug Delivery System (Capsules): Size 9 capsules for preclinical rat studies (Capsu-Gel). Enteric Coating EudragitL-100-55 (Hulls America, Inc.). Basal 24 hr urine collection. Fecal analysis for *Oxalobacter formigenes*—rats were not colonized with *Oxalobacter formigenes*.

Experimental Protocol:

A. Long-term Studies

Animal Protocol

Group I (n=4): Fed oxalate diet with lysate. Rats were given two capsules everyday at 4:00 p.m. and oxalate diet overnight. Diet was removed during the day (8:00 a.m. to 4:00 p.m.)

Group II (n=4): Fed oxalate diet as described for Group I (Hyperoxaluric Controls).

24 hr urine samples were collected on Day 7 and Day 9 of the above treatment.

Data on the mean urinary oxalate concentration for the two groups of rats shown above indicated that feeding of Oxalobacter lysate lowered the urinary oxalate concentration in Group I rats as compared to the hyperoxaluric controls (Group II). The enzymes can not be active for a long duration in the gastrointestinal tract; therefore, short-term studies were performed as described below.

B. Short-term Studies

Animal Protocol

Group I (n=4): Fed 1 capsule at 8:00 a.m.; oxalate diet for two hours (rats were fasted overnight so that they eat well during this period) and 1 capsule at 10:00 a.m.

Group II (n=4): Oxalate diet for two hours as for Group I. Urine was collected from all the animals for the next five-hour period and analyzed for oxalate concentration. This was performed on days 11, 12 and 15 of this study.

The results of this study show that feeding the Oxalobacter lysate produces a significant decrease in urinary oxalate levels in a 5 hour period after oxalate and drug administration in Group I rats as compared to the hyperoxaluric control group (Group II). At this point a crossover study between the two groups of rats was performed.

C. Cross-Over Studies
Animal Protocol
Group I: Fed oxalate diet twice a day at 8:00–10:00 a.m. and 3:00 p.m–5:00 p.m.
Group II: Fed 1 capsule twice a day before feeding the oxalate diet as for Group I.

Short-term studies for the effect of oxalobacter lysate feeding on urinary oxalate levels were performed as described in Section-B above on day-2 and day-5 after the cross-over.

Crossover studies show that previously hyperoxaluric Group II rats, which are now being fed the Oxalobacter lysate, show a decline in urinary oxalate levels. In contrast the Group-I rats revert to hyperoxaluria upon withdrawal of the drug.

EXAMPLE 4

Treatment with *Oxalobacter formigenes* Cells to Rats

A study was conducted to evaluate the fate of dietary oxalate when *Oxalobacter formigenes* cells are included in the diet.

Methods

Male Wistar rats were fed a normal calcium (1%), high oxalate (0.5%) diet, or a low calcium (0.02%), high oxalate diet (0.5%) diet during two separate experiments. $^{14}$C-oxalate (2.0 uCi) was given on day 1 and again on day 7 of the study. *Oxalobacter formigenes* cells (380 mg/d) were administered in rat drinking water on days 5–11. The fate of $^{14}$C from oxalate was measured based on analysis of $^{14}$C in feces, urine and expired air. The rats served as self controls and measurements during the control period (before Oxalobacter cells were fed) were made during days 1–4; during the experimental period (when bacterial cells were fed) measurements were made on days 7–11.

Figure 1B:
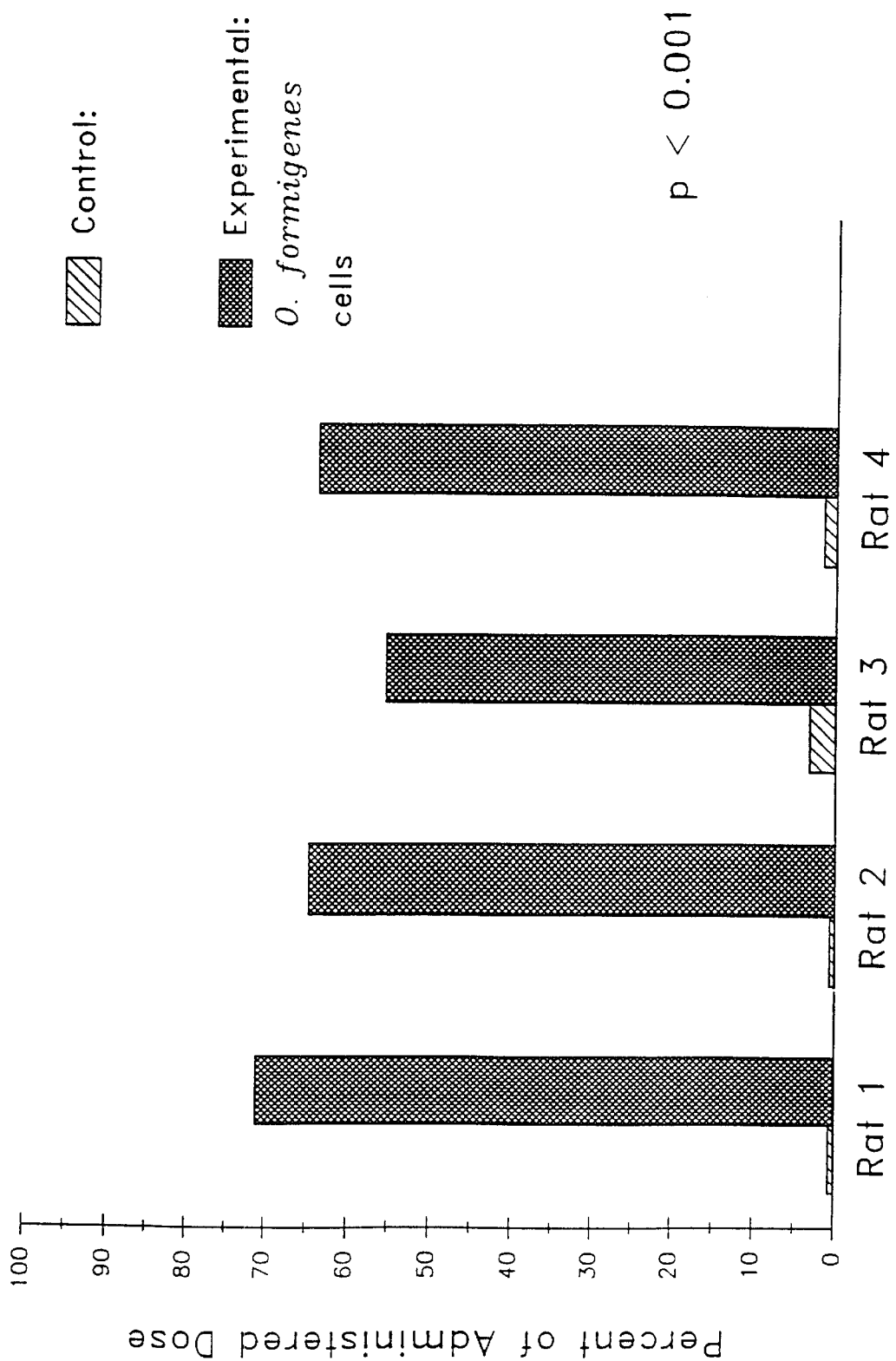
FIG. 1b shows the results of a study evaluating the conversion of labeled carbon (C-14) from dietary oxalate into carbon dioxide when *Oxalobacter formigenes* cells are fed to rats on a low calcium diet.

Results:

1. When rats were fed the normal (1%) calcium diet, less than 1% of the administered dose of $^{14}$C from oxalate was recovered in expired air (as carbon dioxide produced from $^{14}$C oxalate in the intestine, absorbed into blood and then expired) however in all cases more of the $^{14}$C was recovered during the period when rats were fed Oxalobacter cells (FIG. 1a) This is in contrast to results obtained when the diet was low in calcium (0.02%) when more than 50% of the $^{14}$C from oxalate was recovered as carbon dioxide in expired air during the experimental period when rats were fed Oxalobacter cells (FIG. 1b). These results are strikingly different from the very low quantities of $^{14}$C (less than 5%) recovered during the control period (before the feeding of Oxalobacter cells). Thus feeding *Oxalobacter formigenes* cells to rats markedly increased the amount of dietary oxalate that was degraded in the intestinal tract.

Figure 2A:
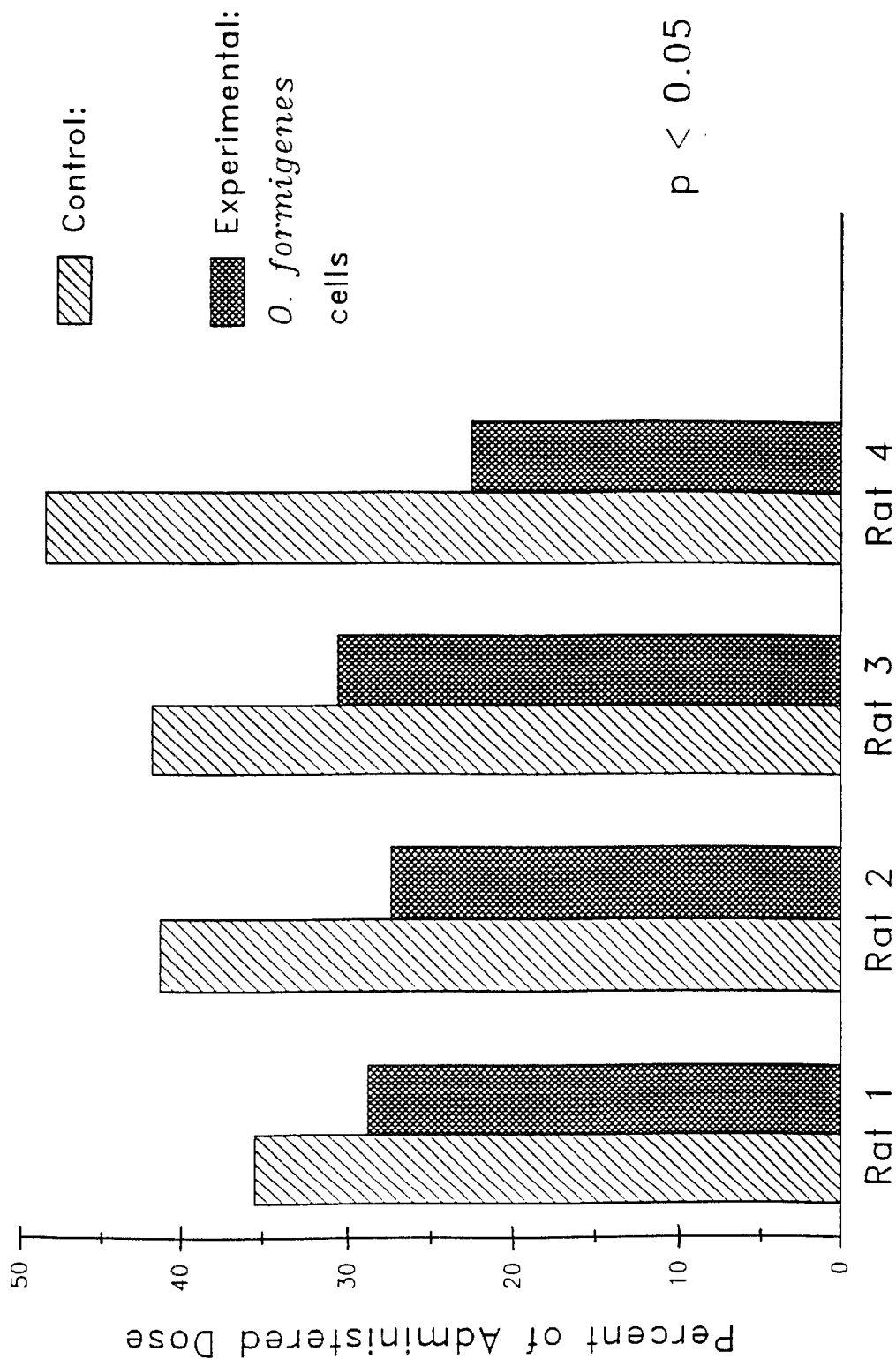
FIG. 2a shows the results of a further study evaluating the fate of dietary oxalate when *Oxalobacter formigenes* cells are included in the diet.
Figure 2B:
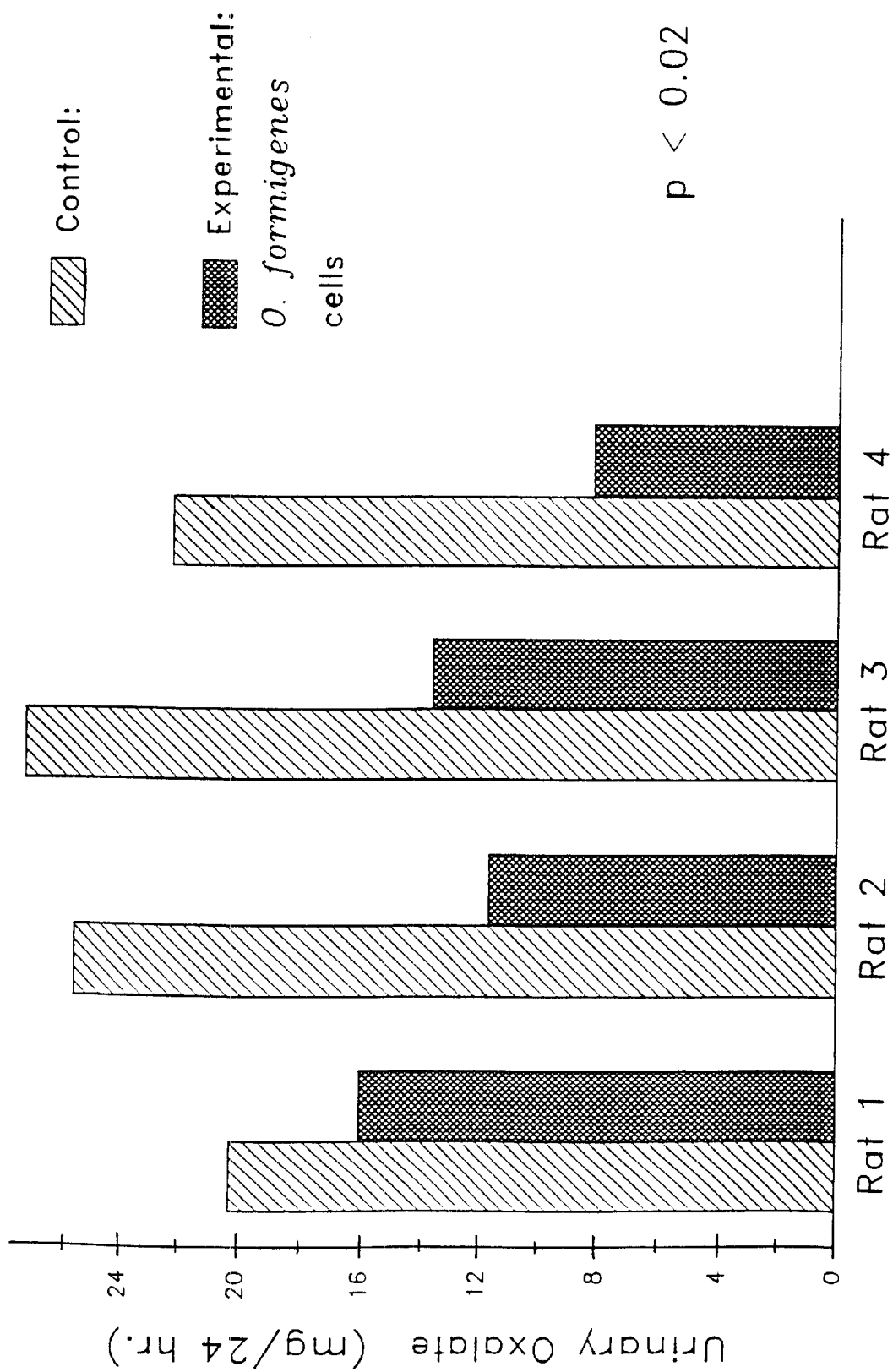
FIG. 2b shows the results of a further study evaluating the fate of dietary oxalate when *Oxalobacter formigenes* cells are included in the diet.
Figure 2C:
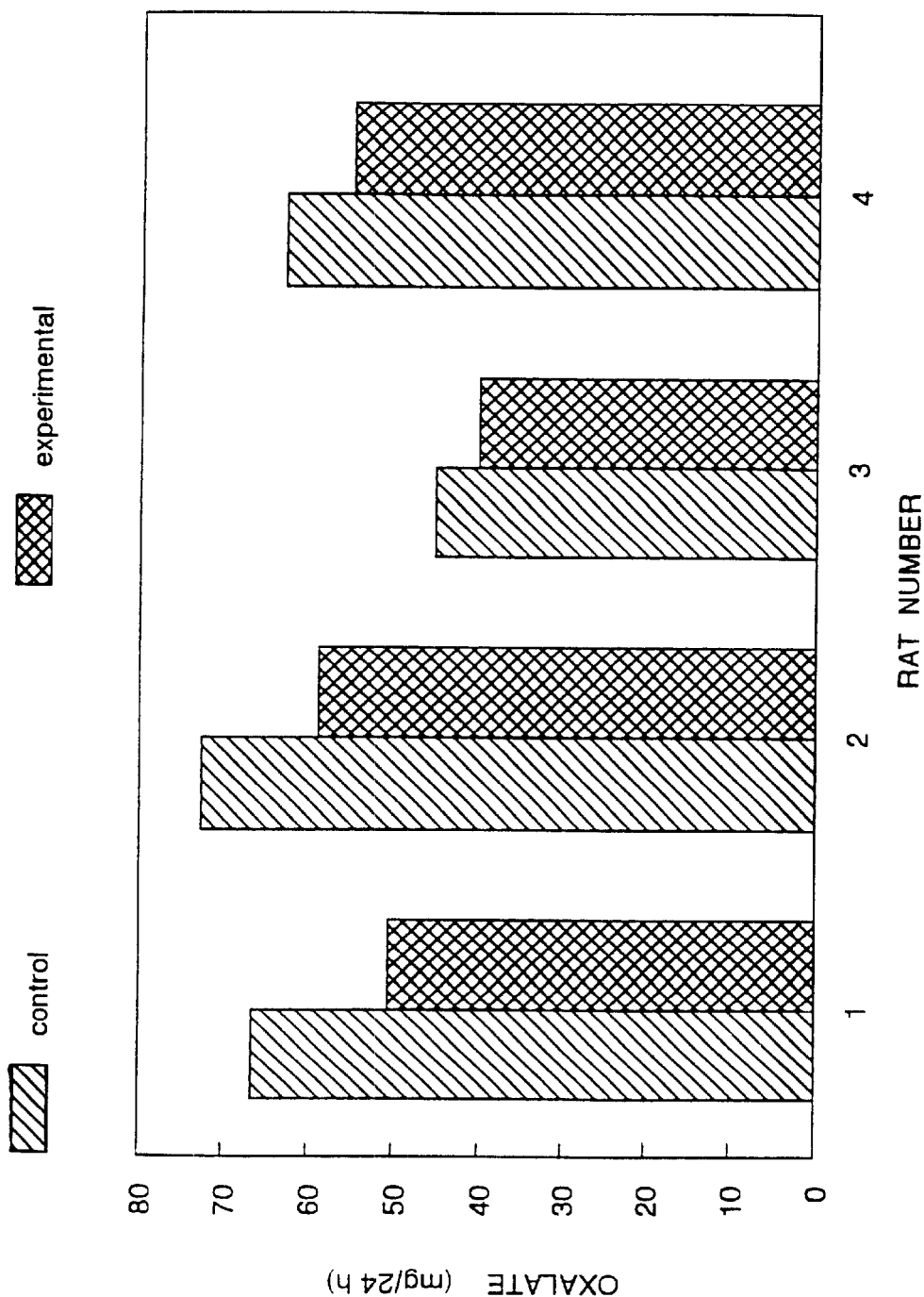
FIG. 2c shows the results of a further study evaluating the fate of dietary oxalate when *Oxalobacter formigenes* cells are included in the diet.

2. Feeding Oxalobacter cells also decreased the amount of $^{14}$C-oxalate that was excreted in urine. Values for a 4 day collections during both the control and experimental periods and for a single day in each of these periods are shown in FIGS. 2a and 2b respectively. Quantities of oxalate recovered in rat feces were also lower during the experimental period (when Oxalobacter cells were fed) than was found for the control period (FIG. 2c).

Most laboratory rats do not carry Oxalobacter in their intestinal tracts (they are not colonized). The present results show that purposeful administration of these oxalate-degrading bacteria to rats causes a large portion of the dietary oxalate to be degraded and that consequently less of the oxalate from the diet is excreted in urine.

The effects of dietary calcium on oxalate degradation are marked. Calcium complexes with oxalate so that its solubility and availability for attack by Oxalobacter is limited and the amount that is degraded when rats are fed a high calcium diet is much less than amounts degraded when calcium in the diet is low.

EXAMPLE 5

Effect of Feeding *O. formigenes* on Urinary Oxalate Excretion in Pigs

Figure 3A:
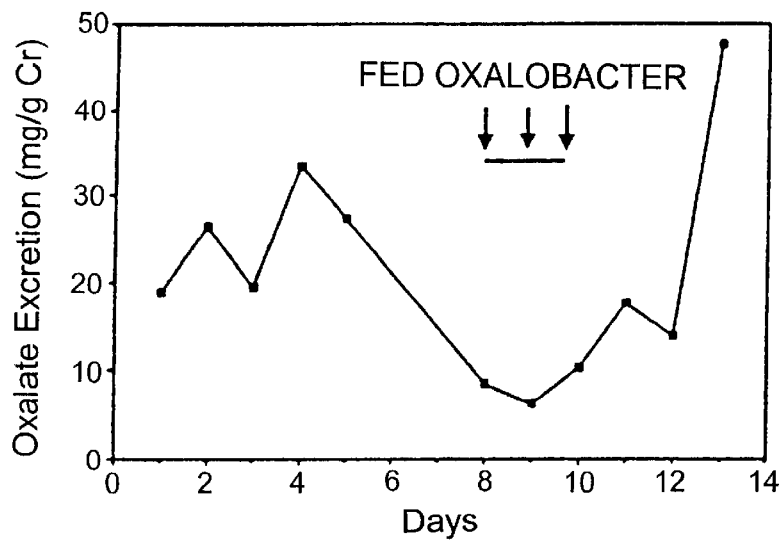
FIGS. 3a–c show the reduction in urinary excretion of oxalate in pigs which are fed oxalobacter.
Figure 3B:
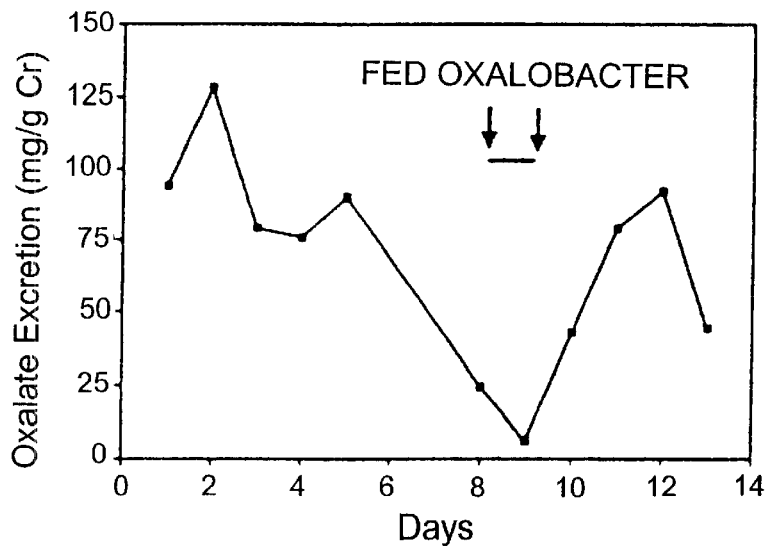
Figure 3C:
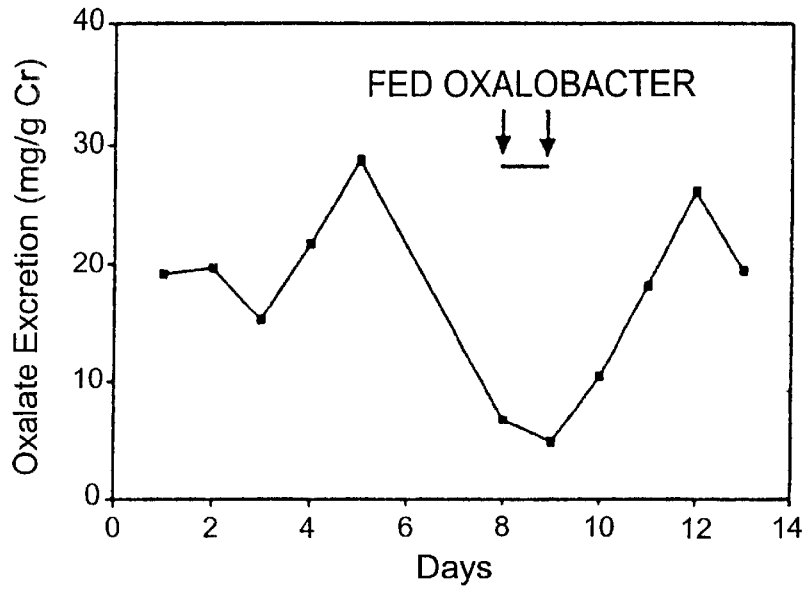

Pigs are naturally colonized with Oxalobacter. Decolonization was achieved in experimental pigs by antibiotic supplementation of the diet. Pigs were fed Oxalobacter in culture broth, which they readily consumed. The pigs were fed a soybean/corn based feed supplemented with 1300 mg oxalate/kg. The basal diet contained 680 mg oxalate/kg. Results are shown in FIGS. 3a–c for three individual pigs.

In all the three pigs urinary oxalate was dramatically decreased during the consumption of Oxalaobeter. The level of excretion of oxalate in these pigs decreased to a minimum of approximately 6 mg/g creatinine in all three pigs. This is to be compared with a level of 8–10 mg/g creatinine that has been observed in humans taking oxalate-free formula diets. This level is equated to the endogenous synthesis in humans as the dietary load has been eliminated. It appears that this level reflects endogenous synthesis in pigs and that the intestinal absorption has been eliminated by Oxalobacter treatment. Furthermore, these results indicate that the ingested Oxalobacter were able to remove both the crystalline oxalate added and the food-borne oxalate that was bioavailable.

In this experiment each pig was fed 1.0 g of cell paste with the morning meal. At O.D.$_{600}$ of 0.6, viable cell count is $2.1 \times 10^8$ cells/ml, which extrapolates to $2.1 \times 10^{13}$ cells per 100 L. The 100 L fermenter run provides us on the average 50–60 gm wet wt of cells. Therefore, 1 gm wet wt of cells is about $3.5 \times 10^{11}$ viable cells.

The dose of $3.5 \times 10^{11}$ viable cells as indicated above could eliminate intestinal absorption of about 2.0 gm of oxalate present per kg diet (1300 mg added oxalate+680 mg present in the diet). The animals consumed 1 kg diet per meal.

The body weight of the pigs is about 200 lbs. and the digestive system of the pigs is believed to be very close to that of humans. In humans the average daily consumption of oxalate is about 100–400 mg depending on the diet composition which is also split into three meals/day, therefore on an average a daily dose of $10^8$ to $10^{10}$ viable cells would be sufficient to prevent the dietary absorption of oxalate.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for reducing oxalate concentrations in an animal wherein said method comprises administering a composition comprising a material selected from the group consisting of an oxalate-reducing effective amount of oxalate-degrading microbes and oxalate-degrading enzymes.

2. The method, according to claim 1, wherein said method comprises administration of oxalate-degrading enzymes.

3. The method, according to claim 2, wherein said oxalate-degrading enzymes are derived from bacteria.

4. The method, according to claim 3, wherein said oxalate-degrading enzymes are derived from bacteria of the group consisting of Clostridium, Pseudomonas, and oxalobacter.

5. The method, according to claim 2, wherein said enzymes are produced recombinantly.

6. The method, according to claim 5, wherein said enzymes are produced recombinantly in *Escherichia coli*.

7. The method, according to claim 2, which comprises administering formyl-CoA transferase and oxalyl-CoA decarboxylase.

8. The method, according to claim 7, wherein said enzymes are produced recombinantly.

9. The method, according to claim 2, wherein said oxalate-degrading enzymes are expressed in plants which have been transformed with polynucleotides encoding said oxalate-degrading enzymes.

10. The method, according to claim 1, wherein said method comprises administration of oxalate-degrading microbes.

11. The method, according to claim 10, wherein said oxalate-degrading microbes have been transformed with polynucleotides which encode said oxalate-degrading enzymes.

12. The method, according to claim 2, which further comprises administering an additional factor selected from the group consisting of oxalyl CoA, $MgCl_2$ and TPP.

13. The method, according to claim 10, which comprises administering whole viable oxalate-degrading microbes.

14. The method, according to claim 13, wherein said microbes are *Oxalobacter formigenes*.

15. The method, according to claim 13, wherein said microbes are selected from the group consisting of Clostridium and Pseudomonas.

16. The method, according to claim 13, wherein said microbes colonize the intestines.

17. The method, according to claim 1, which is used to treat a patient whose intestines have insufficient numbers of oxalate-degrading bacteria.

18. The method, according to claim 17, which is used to treat a patient whose natural intestinal bacteria have been depleted due to treatment with antibiotics.

19. The method, according to claim 1, which is used to treat a domesticated animal, said animal having deficient numbers of oxalate-degrading bacteria.

20. The method, according to claim 19, wherein said domesticated animal is selected from the group consisting of dogs, cats, rabbits, ferrets, guinea pigs, hamsters and gerbils.

21. The method, according to claim 19, wherein said domesticated animal is an agricultural animal.

22. The method, according to claim 21, wherein said agricultural animal is selected from the group consisting of horses, cows and pigs.

23. The method, according to claim 19, which is used treat a domesticated animal, said animal's natural intestinal bacteria having been depleted due to treatment with antibiotics.

24. The method, according to claim 1, wherein said microbe or said enzyme is formulated to reduce inactivation in the stomach.

25. The method, according to claim 24, wherein said formulation comprises a coating which dissolves preferentially in the small intestine compared to the stomach.

* * * * *

UNITED STATES PATENT AND TRADEMARK OFFICE
CERTIFICATE OF CORRECTION

PATENT NO. : 6,355,242 B1
DATED : March 12, 2002
INVENTOR(S) : Milton J. Allison and Harmeet Sidhu It is certified that error appears in the above-identified patent and that said Letters Patent is hereby corrected as shown below:

Column 1,
Line 45, "urinarytract" should read -- urinary tract --.

Column 2,
Lines 2 and 6, "degradingbacteria" should read -- degrading bacteria --.
Line 16, "*Oxalabacterformigenes*" should read -- *Oxalabacter formigenes* --.
Line 17, "degradinganaerobes" should read -- degrading anaerobes --.
Line 20, "Comick" should read -- Cornick --.

Column 3,
Line 39, "degradingenzymes" should read -- degrading enzymes --.

Column 5,
Line 50, "degradingenzymes" should read -- degrading enzymes --.

Column 6,
Line 52, "degradingbacteria" should read -- degrading bacteria --.

Signed and Sealed this

Eleventh Day of February, 2003

JAMES E. ROGAN
*Director of the United States Patent and Trademark Office*